(12) United States Patent
Gardner et al.

(10) Patent No.: US 7,829,532 B2
(45) Date of Patent: *Nov. 9, 2010

(54) METHOD OF TREATING A NERVE-RELATED VISION DISORDER IN A NON-DIABETIC SUBJECT

(75) Inventors: Thomas W. Gardner, Hummelstown, PA (US); Chad E. Reiter, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 356 days.

This patent is subject to a terminal disclaimer.

(21) Appl. No.: 11/755,232

(22) Filed: May 30, 2007

(65) Prior Publication Data

US 2007/0270345 A1  Nov. 22, 2007

Related U.S. Application Data

(63) Continuation of application No. 10/375,973, filed on Feb. 28, 2003, now Pat. No. 7,247,702.

(60) Provisional application No. 60/361,559, filed on Feb. 28, 2002.

(51) Int. Cl.
*A61K 38/28* (2006.01)
*A61F 2/00* (2006.01)

(52) U.S. Cl. .......................... 514/3; 530/303; 424/427

(58) Field of Classification Search ...................... None
See application file for complete search history.

(56) References Cited

U.S. PATENT DOCUMENTS

| 5,182,258 A | 1/1993 | Chiou |
| 5,457,109 A | 10/1995 | Antonucci et al. |
| 6,090,839 A | 7/2000 | Adams et al. |
| 6,160,000 A | 12/2000 | Adams et al. |
| 2005/0208103 A1 | 9/2005 | Adamls et al. |

OTHER PUBLICATIONS

Bosco et al., Invest. Opthal. Vis. Sci. 49: 1437-1446, 2008.*
Klein et al., Arch. Opthol. 102: 520-526, 1984.*
J. Ambatl; C. Canakls; J.Miller; E. Gragoudos; A. Edwards; D. Wolssgold; I. Kim; F. Delari; A. Adamls, "Diffusion of High Molecular Weight Compounds through Sclora," IOVS, Apr. 2000, vol. 41, No. 5. pp. 1181-1185.
J. Ambatl; E. Gragoudas; J. Miller; T. You; K. Miyamoto; F. Delori; A. Adamls, "Transscloral Delivery of Bioactive Protein to the Chorold and Retina," IVOS, Apr. 2000, vol. 41, No. 5, pp. 1188-1191.

* cited by examiner

*Primary Examiner*—Robert Landsman
*Assistant Examiner*—Gyan Chandra
(74) *Attorney, Agent, or Firm*—Gifford, Krass, Sprinkle, Anderson & Citkowski, P.C.

(57) ABSTRACT

This invention provides reagents and methods for delivering insulin, insulinomimetic agents, and the like to a vertebrate eye via subconjunctival routes, sub-Tenon's routes, or intravitreal routes for treatment of nerve-related vision disorders such as diabetic retinopathy, and formulations useful in the practice of the disclosed methods.

4 Claims, 5 Drawing Sheets

METHOD OF TREATING A NERVE-RELATED VISION DISORDER IN A NON-DIABETIC SUBJECT

REFERENCE TO RELATED APPLICATION

This application is a continuation of U.S. patent application Ser. No. 10/375,973, filed Feb. 28, 2003, now U.S. Pat. No. 7,247,702, which claims the benefit of U.S. Provisional Application Ser. No. 60/361,559, filed Feb. 28, 2002, the entire content of all of which is incorporated herein by reference.

BACKGROUND OF THE INVENTION

1. Field of the Invention

This invention relates generally to a method for delivering insulin, insulinomimetic agents, and the like to the eye for treatment of diabetic retinopathy. More specifically, the method involves the periocular administration of these drugs via subconjunctival routes, sub-Tenon's routes, or intravitreal routes.

2. Background of the Related Art

Diabetes has reached epidemic proportions. Approximately 15 million people in the United States are currently afflicted with the disease, and that number is expected to rise to at least 21 million over the next 30 years.

In addition to (and as a consequence of) the metabolic disarray caused by the disease, diabetes causes a variety of other, organ-specific dysfunctions, including in particular diabetic retinopathy. Diabetic retinopathy affects half of all Americans diagnosed with diabetes. Diabetic retinopathy is an illness that occurs when diabetes damages tiny blood vessels in the retina, affecting vision, and is a leading cause of blindness. There are two clinical stages of retinopathy. The first stage is known as nonproliferative retinopathy, in which the blood vessels damaged by diabetes leak fluid and lipids onto the retina. When the fluid accumulates in the center of the retina (i.e., the macula) it leads to macular edema. The fluid makes the macula swell, which blurs vision. The second stage is the proliferative stage, where new blood vessels grow along the retina and in the clear, gel-like vitreous that fills the inside of the eye. These new blood vessels can bleed, cloud vision, and destroy the retina unless treated. There is also a preclinical phase in which patients will generally have no symptoms, nor will there be any findings on routine clinical examination. However, in the preclinical phase sensitive tests reveal reduced contrast sensitivity, electrical responses with an electroretinogram, or color vision.

There are several methods of treatment for diabetic retinopathy disclosed in the art. However, none of these treatment approaches have proven successful in addressing the primary metabolic disorder or in preventing retinopathy. Conventional diabetic retinopathy treatments are limited to controlling the diabetic state with systemic insulin administration or oral hypoglycemic agents. The problem with these systemic approaches is that they do not restore normal physiologic metabolic control or provide overall effective levels of the drug to the eye. Secondary treatment approaches include using diuretics to control blood pressure or intravascular fluid overload. Attempts have also been recognized in the arts for treating retinopathy with aldose reductase inhibitors, inhibitors of nonenzymatic glycation (aminoguanidine), corticosteroids or antihistamines. Methods of treatment for advanced retinopathy complications include vitrectomy surgery and laser treatment, exposing an intense beam of light to the small diseased areas of the retina. These methods are palliative in nature, and none of these methods is sufficiently effective to prevent or cure the disease.

Although diabetic retinopathy is extensively studied in the art, the direct effects of insulin or insulinomimetics on diabetic retinopathy are limited. It has been demonstrated that retinal neurons die in experimental diabetes in rats and in humans. Moreover, insulin has been shown to be a survival factor for retinal neurons in culture, and excess hexosamines impair insulin's survival-promoting effects. In vivo, systemically and intraocularly administered insulin activates the insulin receptor and downstream signaling cascades that are involved in cell function and survival. However, the ability to administer systemically sufficient insulin or other insulinomimetic agents to be effective for prevention of retinopathy is limited by the risk of hypoglycemia.

Accordingly, there is a great demand for safe and effective methods for delivering agents effective in treating diabetic retinopathy. In particular, there is a need in the art for treatment methods that maintain retinal cell function and survival in the face of persistent hyperglycemia.

SUMMARY OF THE INVENTION

The invention describes methods and reagents for treating retinal disorders, particularly retinal disorders having at least in part a metabolic etiology. As provided herein, the inventive methods and reagents permit compounds for treating ocular disorders, such as retinal detachment, retinitis pigmentosa, central retinal artery occlusion, central retinal vein occlusion, ischemic optic neuropathy, high tension glaucoma, low tension glaucoma, and cataract, to be administered locally in the eye. The invention specifically provides methods for preventing and treating nerve-related vision disorders, including in particular diabetic retinopathy. The inventive methods comprise periocular administration of a sufficient amount of a drug by a subconjunctival, sub-Tenon's or intravitreal route to be effective in treating such retinal disorders. In certain embodiments, the drug is administered to an eye under its mucous membrane or fascia.

Preferred drugs administered using the methods of the invention include formulations of insulin, insulinomimetic agents, or peptides. Formulations of insulin that may be used in the invention include, for example, formulations of native insulin, naturally derived insulin, recombinant insulin, any modification thereof containing buffers or modifying proteins, or any other known formulations of insulin. The concentration of the insulin formulation can range from 1 picomolar to 100 micromolar. If the insulin formulation is a gel or liquid, the volume thereof can range from 5 μL to 1 mL. In the practice of the inventive methods, a sufficient amount of any of these drugs is administered to the eye, wherein a sufficient amount of insulin ranges from 5 to 100 μL or 0.1 to 10 units of insulin. Formulations can also include augmenting drugs from the thiazolidinediones (TZD) class, such as rosiglitazone, pioglitazone, and troglitazone, as well as, non-peptide insulinomimetic agents, such as TLK16998 (Telik), KRX-613, and L-783,281 (Merck).

The invention further comprises methods of administrating drugs to the eye, where drugs are administered to more than one eye. These methods of administration include via a solution, a polymeric base, or a pump. Additionally, the method of administration may be by implanting a device, where the device releases a formulation of a drug, preferably insulin, an insulinomimetic agent or a peptide at a prescribed rate. One or more devices may be administered to one eye.

The invention also provides formulations of insulin, insulinomimetic agents or peptides adapted or prepared for use with the methods of the invention. Preferably, the formulations of the invention comprise pharmaceutical adjuvants, carriers, buffers or other components.

Specific preferred embodiments of the present invention will become evident from the following more detailed description of certain preferred embodiments and the claims.

DETAILED DESCRIPTION OF PREFERRED EMBODIMENTS

Figure 1:
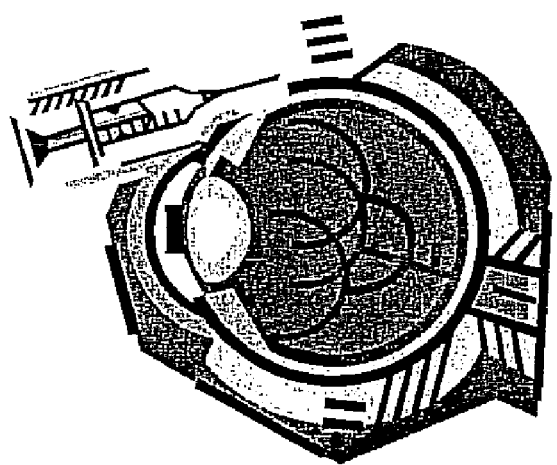
FIG. 1 illustrates the invention's method for administration of drugs under the eye's surface membrane.

The invention provides reagents, pharmaceutical compositions and methods for delivering drugs for treatment or prevention of nerve-related vision disorders, particularly diabetic retinopathy. The method specifically comprises periocular administration of insulin, insulinomimetic agents or peptides via subconjunctival, sub-Tenon's or intravitreal routes.

More specifically, the method of the invention comprises periocularly administering a sufficient amount of a formulation of insulin, insulinomimetic agents or peptides to both eyes. Periocular delivery is safer for the general health of an animal, preferably a human, undergoing treatment for a nerve-related vision disorder since it involves less ocular morbidity than laser or vitrectomy surgery.

The ability to systemically administer sufficient amounts or concentrations of insulin or other insulinomimetic agents to prevent retinopathy is largely limited by the risk of hypoglycemia. The invention overcomes the consequences of systemic administration by achieving direct local drug delivery of effective amounts of these agents by direct administration to the subconjunctiva, sub-Tenon's capsule, or intravitreous. Administering insulin or insulinomimetic agents via these routes also provides effective intraocular drug penetration to maintain retinal cell function and survival.

One aspect of this invention involves replacing a deficient insulin receptor ligand and increasing activation of a downregulated insulin receptor, or its downstream signaling molecules. Specifically, the inventive methods comprise direct insulin administration to the eye, and specifically to cells of the retina. Any pharmaceutically acceptable insulin formulation can be used with the methods of the invention. Examples of useful insulin formulations include native insulin (preferably human insulin, particularly recombinantly-produced human insulin such as Humulin®, or insulin isolated from any other mammalian species), naturally derived or recombinant, and all of modifications thereof, such as Regular to NPH, Ultralente (Eli Lilly & Co.), insulin glargin (Lantus®, Aventis), Lispro®, (Eli Lilly & Co.), Novolin® (Novo-Nordisk) and formulations containing any modifying proteins (such as, for example, prolamine) or buffers known or accepted in the art.

Moreover, the invention provides methods comprising administration of insulinomimetic agents or nucleotides (aptamers) that mimic some or all of insulin's actions. The invention further encompasses the administration of drugs that augment insulin along with the insulin. These augmenting drugs can be, inter alia, from the thiazolidinediones (TZD) class. They may also be small non-peptide insulinomimetic agents such as TLK16998 (Telik), KRX-613, and L-783,281 (Merck). Such compounds activate the proliferator-activator gamma (PPAR-gamma) receptor to provide necessary actions of insulin in the retina. Thus, their addition enhances the insulin effect on signaling to retina cells. Examples of augmenting drugs include rosiglitazone, pioglitazone, and troglitazone.

Concentrations of the drugs used in the invention can range from low picomolar to micromolar concentrations. If the drug is a liquid or gel insulin formulation, volumes can range from about 10 μL to about 1 mL. A sufficient dosage of the insulin will range from a few picomolars to micromolar.

The inventive treatment provided herein permits a number of different administration routes to be used to introduce an effective amount of a drug to the eye. These include administering the drug via a pump, a polymeric base, or a solution. The preferred method of administration is by a polymeric base, including but not limited to polyester (PET), polyethylene (PE), poly(L-lactic acid) (PLA), and polyurethane. Additionally, drugs may be administered by implantation of a formulation of the invention or a device that will release such a formulation at a prescribed rate. The invention advantageously provides methods for administering said formulation to both eyes simultaneously, although embodiments having administration to one eye, as well as embodiments having independent or non-contemporaneous administration to both eyes, are also encompassed by the invention.

Drug formulations of the invention advantageously can be administered under the mucous membrane of the eye or the Tenon's fascia of the eye. More specifically, the drugs can be delivered to the subconjunctival and/or sub-Tenon's space.

As shown in FIG. 1, drug formulations of the invention are injected, or otherwise administered, under the eye's surface membrane so that the drugs are able to diffuse through the sclera into the retina, vitreous, and the anterior chamber.

The inventive methods for treatment of nerve-related retinal disorders, such as diabetic retinopathy, are suitable for prevention or treatment at any stage of such retinopathic disorders. Specifically, the inventive methods are equally effective for the preclinical, nonproliferative, macular edema stages of such retinopathic disorders, as well as for the proliferative stage of retinopathy. Other retinal disorders advantageously treated using the methods of the invention, include retinal detachment, glaucoma, retinitis pigmentosa, central retinal artery or central retinal vein occlusion, ischemic optic neuropathy, high tension glaucoma, low tension glaucoma, and cataract.

While the invention has been described with particular reference to diabetic retinopathy treatment and other retinal disorders, it will be understood by those skilled in the art that the invention has applications in other medical fields, in particular whenever local insulin or insulinomimetic agents are delivered to tissues at risk for complications. For example, deliveries to kidneys and nerves since patients with diabetes have impaired kidney function (nephropathy) and nerve function (neuropathy). Thus, local application of insulin adjacent to these organs and tissues may improve their function and prevent future deterioration.

The following Examples are intended to further illustrate certain aspects of the above-described method and advantageous results. The following examples are shown by way of illustration and not by way of limitation.

Example 1

Intraportal insulin injection was performed to determine if a single bolus insulin injection, and therefore an acute elevation in circulating insulin, could activate retinal insulin receptors (IR) in vivo as it does in other tissues. Intraportal insulin injection was conducted as follows. Male Sprague-Dawley rats (Charles River, Mass.) weighing 200 350 g were fasted 18 hours prior to being anesthetized with a 10:1 ketamine:xylazine cocktail (53.5 mg/kg ketamine and 5.33 mg/kg xylazine) administered by intramuscular injection. The fasted rats were administered a 500 µg bolus of insulin, nothing (sham), or vehicle (0.9% saline) via the portal vein. At 15, 30, 45 and 60 minutes post injection (shown in FIG. 2A), hindquarter skeletal muscle and retina were snap-frozen under liquid nitrogen, and then stored at −80° C. pending analysis by immunoprecipitation and immunoblotting. There was no difference in insulin receptor beta-subunit (IRβ) phosphorylation between vehicle (V) and insulin (I) injection.

Tissue lysates were immunoprecipitated and immunoblotted as described by Barber et al. (2001, *J. Biol. Chem.* 276: 32814 32831). Tissues were homogenized in an immunoprecipitation (IP) lysis buffer (consisting of 50 mM HEPES, pH 7.3, 137 mM NaCl, 1 nM MgCl$_2$, 2 mM NaVO$_4$, 10 mM Na$_2$H$_2$P$_2$O$_7$, 10 mM NaF, 2 mM EDTA, 2 mM PMSF, 10 mM benzamidine, 10% glycerol, 1% NP-40, and 1 protease inhibitor tablet (Boehringer-Mannheim) per 10 mL of buffer. Homogenates were rocked 15 minutes at 4° C. and then centrifuged at 14,000 rpm at 4° C. Prior to immunoprecipitation and immunoblotting, the resulting supernatant was subjected to protein assay (Bio-Rad) and quantification.

Immunoprecipitations were performed as follows. Protein (250 µg) was diluted into 1 mL IP buffer containing one of the following antibodies: 5 µL of anti-IRβ or anti-IGF-IRβ (Santa-Cruz, Santa Cruz), or 4 µL of anti-IRS-1 or IRS-2 (Upstate Biotechnology, Lake Placid, N.Y.), specific for these species of insulin responsive substrate, and 30 µL of a 50% protein A/Sepharose bead slurry (Amersham Pharmacia Biotech, Piscataway, N.J.). The Sepharose bead complex was rocked overnight at 4° C., washed twice with 200 µL of IP buffer, and boiled with 30 µL of 2× sample buffer (a solution of glycerol, SDS, TRIS buffer, bromophenol blue and betamercapto-ethanol). Fifty µg of protein per sample were analyzed by SDS-polyacrylamide gel electrophoresis (SDS-PAGE). Thereafter, gel-separated proteins were transferred to nitrocellulose membranes (blocked with a solution of 0.05% Tween-20 and 5% non-fat milk or 3% bovine serum albumin, dissolved in Tris-buffered saline) at room temperature for 1 hour. The membranes were probed overnight in blocking solution at 4° C. at 1:1000 dilutions of the primary antibody. The primary antibodies used in these assays included an anti-phosphotyrosine antibody (Upstate Biotechnology), and anti-Act antibodies (Cell Signaling, Beverly, Mass.). Secondary antibodies were diluted 1:4000 (for horseradish peroxidase-conjugated anti-rabbit antibodies; obtained from Amersham Pharmacia Biotech, Piscataway, N.J.), or 1:1000 (for biotin-conjugated anti-mouse antibodies; obtained from Amersham Pharmacia Biotech). Tertiary incubations with streptavidin-linked alkaline phosphatase were diluted 1:4000 (Gibco, Gaithersburg, Md.). Positive signals were detected with electrochemiluminescence (ECL) kits (Cell Signaling) and electrochemifluoresence (ECF) kits (Amersham) each performed according to each manufacturer's protocol. Immunoblot quantitation was accomplished using ImageQuant (Molecular Dynamics), NIH Image 1.6 (NIH, or GeneTools (SynGene) software. Blots were re-incubated with different antibodies after being stripped, at 50° C. for 1 hour in a buffer containing 63 mM Tris (pH 6.8), 2% SDS, and 0.07% 2-mercapthoethanol.

Western blots interrogated with anti-phosphotyrosine (PY) antibodies showed a robust response in muscle, as expected. IRβ phosphorylation was also increased in retinal tissue, but only after a 30 minute delay. In addition, the response had a smaller magnitude than muscle. No difference in IRβ phosphorylation was found in sham-operated rats. These results indicated that retinal IRβ has greater levels of basal phosphorylation than muscle in vehicle treated rats.

Figure 2:
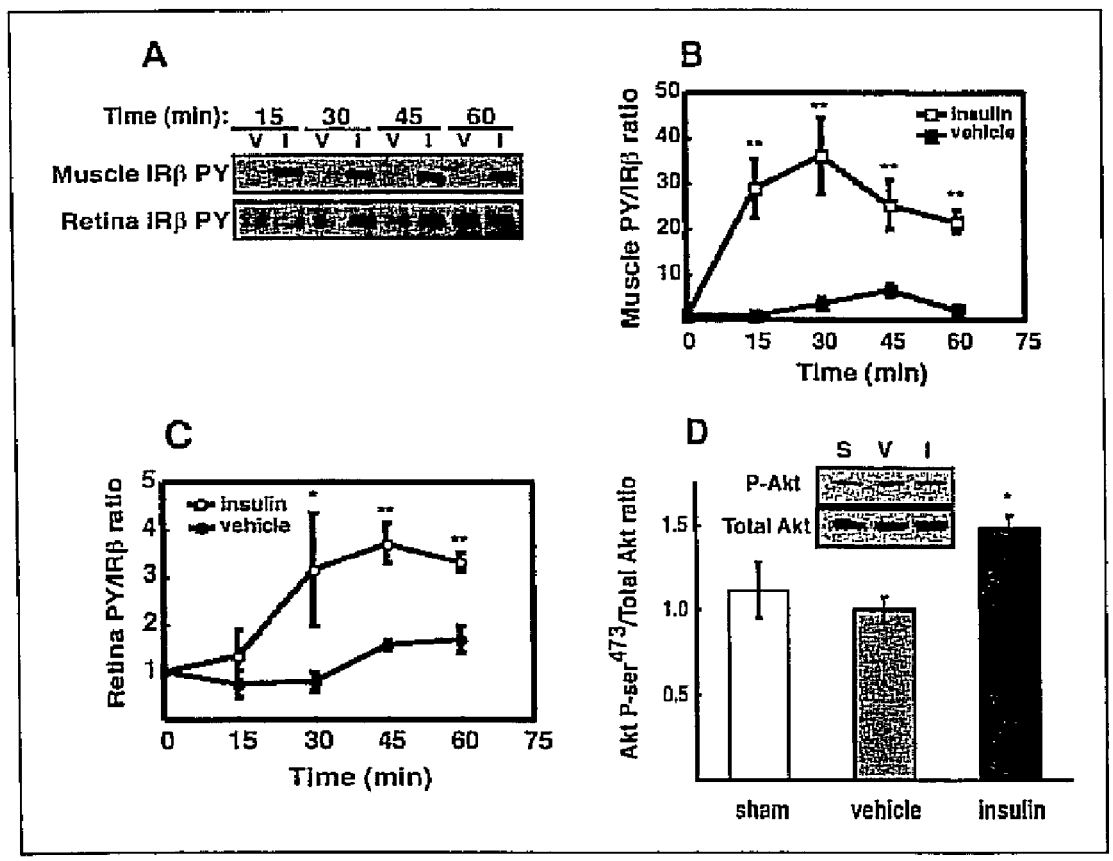
FIG. 2A presents a phosphotyrosine CPY) detecting Western blot from both muscle and retina in a rat that received either a vehicle (V) and insulin (1) injection.
FIG. 2B presents a graph quantifying Western blot analysis and expressing data as a graph for muscle tissue in terms of phosphotyrosine/insulin receptor beta-subunit (PY/IRβ) ratios.
FIG. 2C presents a graph quantifying the Western blots and expressing data as a graph for retina tissue in terms of PY/IRβ ratios.
FIG. 2D presents an immunoblot of phospho-Akt$^{ser473}$ (top) and total Akt (bottom) from vehicle, and insulin injected rats as well as quantification of the blot expressed in terms of phosphorylated to total Akt ratios.

The results of experiments quantifying this Western blot analysis are shown in FIG. 2B, presented as a ratio of phosphotyrosine (PY) levels to insulin receptor beta-subunit (IRβ) amounts (PY/IRβ). In these experiments, Western blots interrogated for muscle PY were stripped, reprobed for total IRβ, quantified and the data expressed in terms of PY/IRβ ratios. The zero time point was set to a ratio of 1. The results in FIG. 2B show a nearly 30-fold increase in phosphotyrosine content in muscle IRβ 15 minutes post-insulin injection, which increase peaked at 30 minutes and declined by 60 minutes post-injection. There was a significant increase in IRβ phosphorylation with insulin at all points examined. FIG. 2C shows the result obtained in parallel experiments performed on retinal tissue. Unlike the results shown in FIG. 2B, tyrosine phosphorylation did not significantly increase in retinal tissue until 30 minutes post injection, was maximal after 45 min and remained elevated 3 4 fold above vehicle-injected controls for 60 minutes. IRβ phosphorylation did not change in vehicle injected animals. The discrepancy in the fold increase in retinal tissue may be due to the relatively higher basal IRβ phosphorylation in the retinas of vehicle treated rats, or to the blood-retinal barrier limiting diffusion of insulin into the retina.

In addition, 45 min after insulin administration retinal lysates were analyzed for Akt activation by Western blotting specifically probed for phosphorylation of Akt (serine 473). These Western blot results, shown in FIG. 2D demonstrated that insulin induced a 48% increase in phosphoserine 473 content of Akt over vehicle injected controls when IRβ phosphorylation is maximal (45 minutes post-injection). Quantification of Western blots, also shown in FIG. 2D indicated there was no statistical difference between sham and vehicle injected controls. These results indicated that systemic insulin injection can effect changes in IRβ phosphorylation in retina, thereby demonstrating that insulin crosses the blood-retinal barrier. Insulin receptor phosphorylation and activation occurs in a different temporal manner than muscle, however, and insulin increases Akt phosphorylation in retina.

Thus, even though insulin penetrates the blood-retinal barrier, the delayed kinetics and lower phosphorylation differential between activated and inactive insulin receptor illustrates the limitations in systemic delivery for affecting retinal diseases related to or dependent on insulin levels, such as diabetic retinopathy.

Example 2

Tyrosine phosphorylation in retinal IRβ and changes therein was compared with other insulin responsive tissues under freely fed and moderately fasted conditions as follows.

Figure 3:
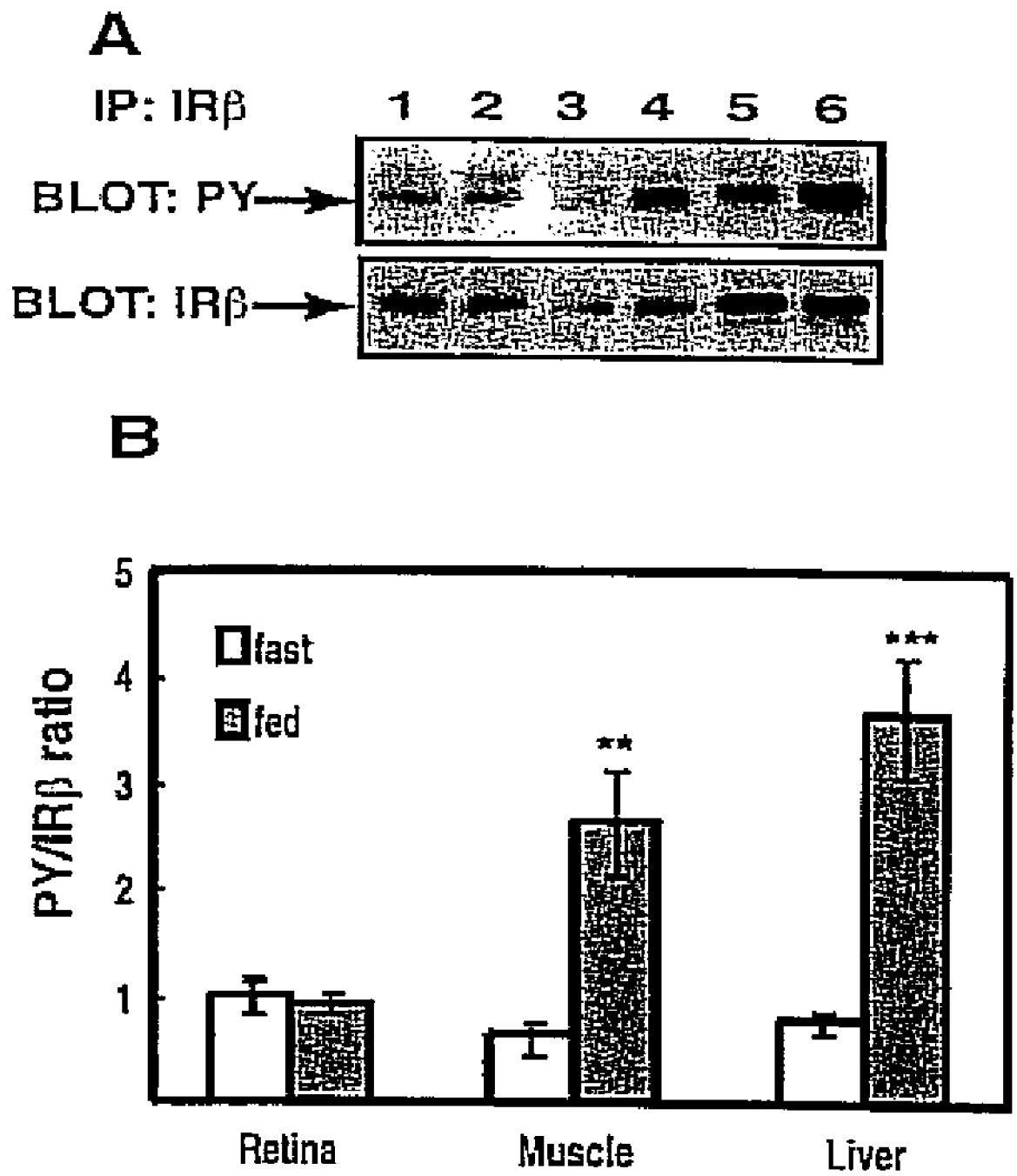
FIG. 3A presents a Western blot comparing IRβ tyrosine phosphorylation in the retina and in other insulin responsive tissues under fasted and freely fed conditions.
FIG. 3B presents a graph quantifying Western blot analyses as disclosed above and expressed as a graph of PY/IRβ ratios for retina tissue.

Six male Sprague-Dawley rats (Charles River) were fasted (18 hours) and were compared to 6 rats that were freely fed overnight. All rats weighed 200 350 g and were anesthetized with a 10:1 ketamine:xylazine cocktail as described in Example 1. Upon loss of motor reflex in the rats' retina, tissue samples from liver and hindquarter skeletal muscle were obtained, homogenized and immunoprecipitated as described in Example 1 and then subjected to Western blot analysis, also as described in Example 1. The blot in FIG. 3A shows that IRβ phosphorylation was unaltered in retina, but increased in muscle and liver compared to fasted rats. Phosphotyrosine-probed immunoblots were then reprobed for total IRβ content with the immunoprecipitating antibody as described in Example 1 to normalize the Western blot data.

The results of these experiments are shown in FIG. 3B as the ratio of PY to total IRβ. Plasma insulin levels were $1.95\pm0.36$ ng/mL in fed rats versus $0.32\pm0.049$ ng/mL in fasted rats (mean.+-.SEM, p=0.011). Similarly, blood glucose levels were $95.5\pm2.6$ mg/dL in fed rats versus $68.83\pm2.4$ mg/dL in fasted rats (mean±SEM, p=0.000008). Image analysis (software from Molecular Dynamics, Sunnyvale, Calif.) of the Western blots from retinal tissue revealed no differences in IRβ phosphorylation between freely fed and fasted rats. In contrast, IRβ phosphorylation in liver and hindquarter skeletal muscle was diminished 23% and 38%, respectively in the fasted rats. On the other hand, IRβ phosphorylation in liver and muscle was significantly greater than in retinal tissue for freely fed rats.

In summary, retinal IR remained relatively constant in response to the physiological levels of insulin in circulation. Phosphotyrosine content of the IRβ in retina did not change, unlike in liver and muscle, despite changes in nutritional status and physiological increases in circulating insulin and blood glucose. IRβ from muscle and liver displayed increased tyrosine phosphorylation as expected in the freely fed state compared to fasted rats. These results were likely due to the fluctuations of circulating insulin in the freely fed condition.

Example 3

Because tyrosine phosphorylation of the IR does not directly measure enzymatic activity, an IR kinase assay was developed.

The IRβ from fasted and fed rats was immunoprecipitated from retina and liver and analyzed by PY immunoblotting for autophosphorylation with (+) and without (−) the addition of ATP to the kinase reaction. IRβ immunoprecipitates obtained as described in Example 2 were subjected to IR kinase assays as follows. The Sepharose bead complex, obtained as described in Example 1, was washed three times with 200 μL of kinase buffer (50 mM HEPES, pH 7.3, 150 mM NaCl, 20 mM $MgCl_2$, 2 mM $MnCl_2$, 0.05% bovine serum albumin, and 0.1% Triton X-100). Western blotting was performed on these immunoprecipitates as described in Example 1; the results of these Western blot experiments (shown below) showed that washing the Sepharose bead/immune complex in kinase buffer did not diminish total bound IRβ. After the last (third) aspiration of kinase buffer, 500 μL of kinase buffer was added with or without 100 μM ATP (Sigma) to each aliquot of the washed Sepharose bead complex. These immune complexes were then rocked at ambient temperature for 1 minute, and the Sepharose beads then collected by brief centrifugation (approximately 3 seconds). The kinase buffer was aspirated, an equal volume of 2× Laemmli sample buffer was added and the samples were boiled for 3 min. SDS-PAGE and phosphotyrosine immunoblotting analysis was performed as described in Example 1.

Figure 4:
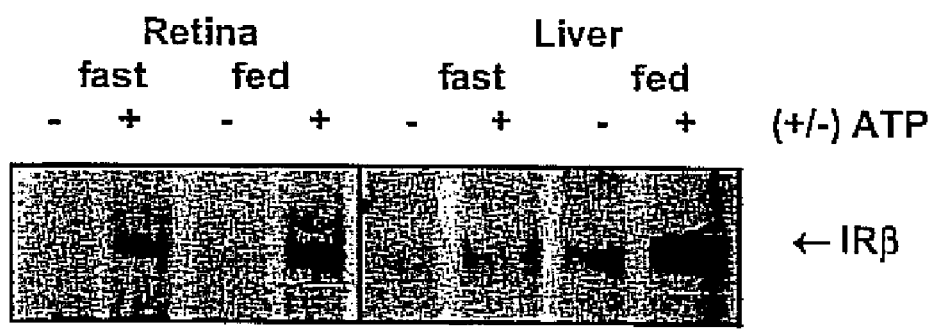
FIG. 4 presents a PY immunoblot for autophosphorylation with (+) and without (−) addition of ATP to the kinase reaction in the retina and liver under freely fed and fasted conditions.

Results of these assays are shown in FIG. 4. The PY immunoblot showed that retinal IRβ displays tonic tyrosine phosphorylation (− lanes), and the rate of phosphate incorporated into the IRβ is not different between fasted and fed rats (+lanes). Liver IRβ, however, displays less basal tyrosine phosphorylation, which increases in the fed state (− lanes). As expected, the rate of IR autophosphorylation is significantly greater in the freely fed rat liver (+lanes, p<0.05).

The results of these Western blot experiments shows that the kinase reaction proceeded linearly though 5 minutes of incubation ($R^2>0.9$) and at a non-limiting dose of 100 μM ATP. The time course of IR autophosphorylation continued to proceed in a linear fashion over the course of these experiments, and the concentration of ATP used did not limit the rate of autophosphorylation.

These results further indicated that there was no change in retinal IRβ autophosphorylation rate between freely fed and fasted rats. These results also suggested a tonic level of tyrosine phosphorylation and kinase activity despite changes in circulating insulin and glucose levels. In contrast, in liver and skeletal muscle IRβ phosphorylation was increased in the freely fed state, leading to a significant increase in autophosphorylation activity. These results thus demonstrated the difference in insulin signaling physiology within the whole animal. Moreover, these results also indicated that the blood-retinal barrier may discretely regulate insulin flux, unlike in tissues that undergo rapid metabolic changes, the results having consequences for insulin administration in diabetic retinopathy.

Example 4

A tissue explant culture system was used to characterize insulin-signaling transduction in retina without the hindrance of the blood retinal barrier present in whole animal models. Such a tissue explant culture system was developed as follows. Rats as described in Examples 1 and 2 were anesthetized using sodium pentobarbital (7.5 mg/kg), and then decapitated upon loss of motor reflexes. Rat retinas were removed by cutting across the cornea, removing the lens, and squeezing the eyeball to rapidly extract the retina. Retinas were pre-incubated in MEM (Sigma) supplemented with 5 mM pyruvate and 10 mM HEPES for 15 minutes at 37° C., 5% $CO_2$, and with gentle shaking. Ten nM insulin or vehicle was added following pre-incubation. At 2, 5, 15, and 30 minutes after insulin addition, retinas were snap-frozen in liquid nitrogen for future use.

Figure 5:
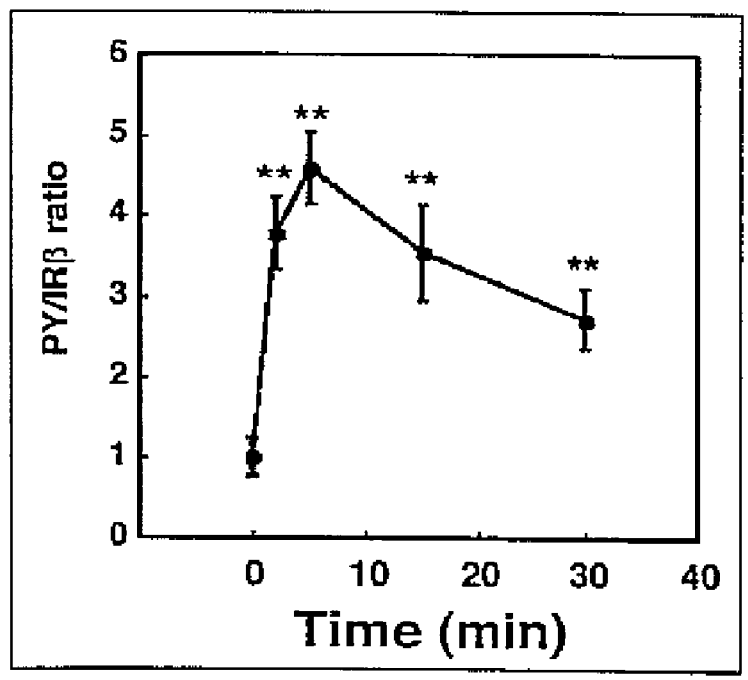
FIG. 5 presents a graph quantifying the Western blots shown in FIG. 4 and expressed as a graph of IRβ activity when IRβ immunoprecipitates were subjected to kinase assays.

To examine the time course of insulin signaling events in the tissue, insulin-treated retinas were compared to retinas that received vehicle (0.9% saline) and to untreated retinas. Tissues were analyzed by immunoprecipitation and Western blotting as described in Example 1. Western blot data were quantified, as shown in FIG. 5, and revealed a significant increase in IRβ phosphorylation at all time points examined when normalized to total IRβ. Within 2 minutes of insulin stimulation, retinal IRβ exhibited a nearly 4-fold greater phosphotyrosine immunoreactivity, which remained elevated at levels 3-fold greater than baseline at the 30 minute time point. This analysis demonstrated that retinal IRβ undergoes increased tyrosine phosphorylation in response to a physiological dose of 10 nM insulin. These results from the explant retina system were similar to the results obtained using a cell culture model.

Figure 6:
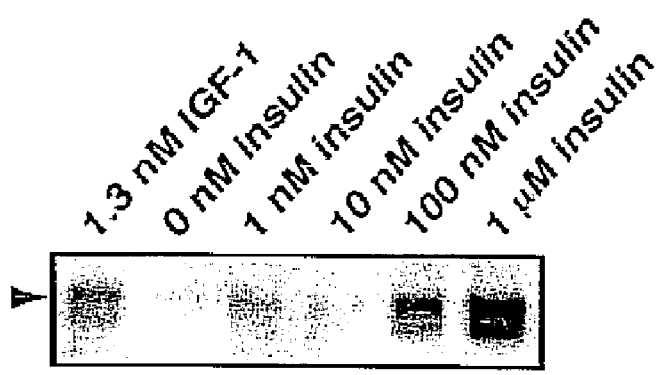
FIG. 6 presents a PY immunoblot for retinas treated with IGF-1 or insulin and subjected to immunoprecipitation of the IGF-1Rβ complex, with the arrowhead indicating the tyrosine phosphorylated band that corresponds to the IGF-1Rβ complex.

Insulin (10 nM) does not activate the IGF-IRβ in retinal explants. Retinas were treated with either 1.3 nM IGF-1 or 0, 1, 10, 100, and 1000 nM insulin, and then retinal lysates were immunoprecipitated with an insulin-like growth factor I receptor (IGF-1Rβ)-specific antibody, followed by PY Western blotting (shown in FIG. 6). The IGF1-R was immunoprecipitated and PY Western blotting performed as described above. Insulin at 100 nM produced similar levels of IGF-IRβ phosphorylation as were found when retinas were contacted with 1.3 nM IGF-1. These results demonstrated that IGF-IRβ phosphorylation remained unchanged in the presence of 10 nM insulin, but increased with 100 nM insulin. These data further indicated that 10 nM insulin does not activate IGF-IRβ in retinal explants, but has specific effects via the IR. Moreover, ATP levels over the time course experiments remained constant, indicating that the energy status of the tissue was not hindering the insulin signaling response.

Figure 7:
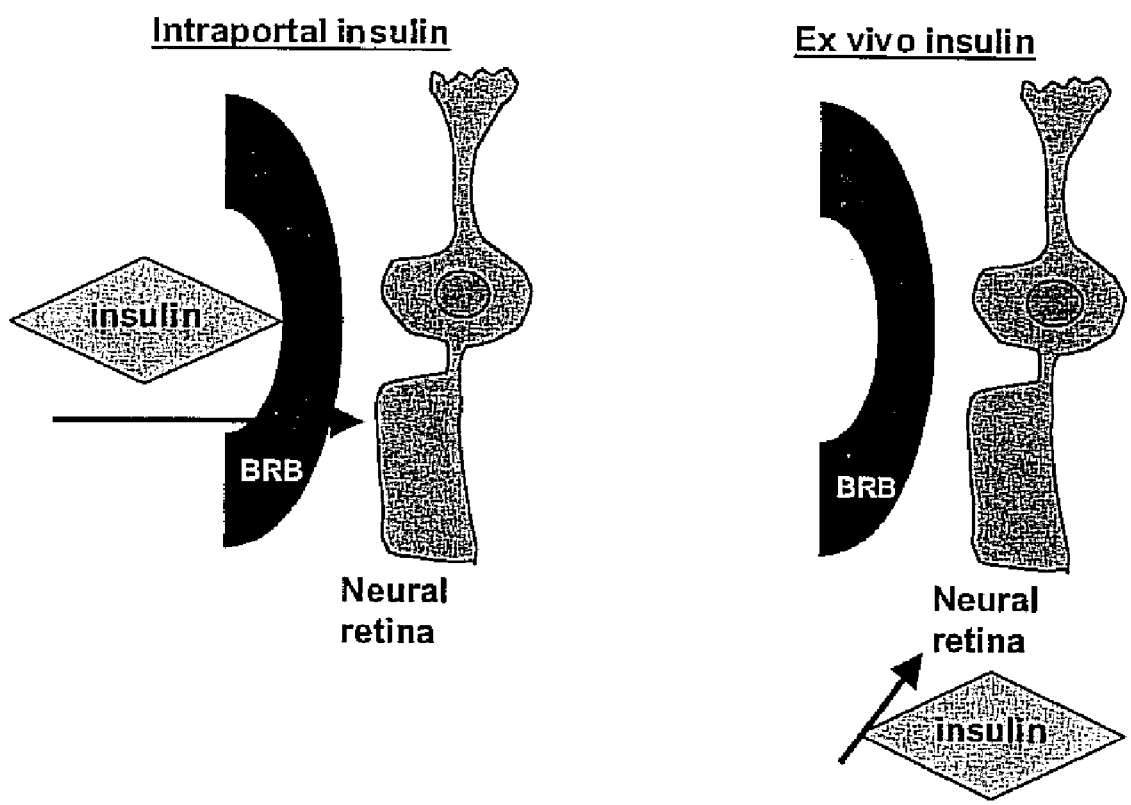
FIG. 7 illustrates the difference between intraportal insulin injection and explanted retina tissue.

These results suggested that isolated retinal tissue can respond robustly to physiological insulin concentrations, this response including IRβ tyrosine phosphorylation. The results also suggested that the blood-retinal barrier plays a significant role in regulating circulating insulin transport since the time course of the response is much faster than observed in vivo. Moreover, intraportal insulin injection experiments (Example 1) showed that insulin's access to the retina is limited by the retinal vasculature, the blood-retinal-barrier (BRB). In explanted retina tissue, in contrast, the BRB is essentially bypassed, and insulin signaling characteristics can be analyzed in a shorter time frame since insulin has direct access to the retina. A schematic comparison of intraportal insulin injection and explanted retina tissue is shown in FIG. 7.

Example 5

In clinical diabetes, hypoglycemia is the major factor that limits the ability of patients to achieve the degree of intensive control of glycemia needed to prevent or reduce retinopathy. Retinal cells die by apoptosis in diabetes, and insulin is a survival factor for retinal neurons acting via the PI3-kinase/Akt pathway, which is inhibited by hyperglycemia. Systemically administered insulin activates the retinal insulin receptor, and the activities of the retinal insulin receptor, PI3-kinase and Akt are reduced after 4 weeks of streptozotocin-induced diabetes. Thus intensive insulin therapy has direct effects on retinal cell survival and function. Since intensive insulin therapy cannot be achieved by most patients due to the hypoglycemic effects of systemic insulin administration, direct application of insulin to the eye can provide the survival effects needed to maintain retinal cell health in the presence of imperfectly controlled systemic diabetes.

Figure 8:
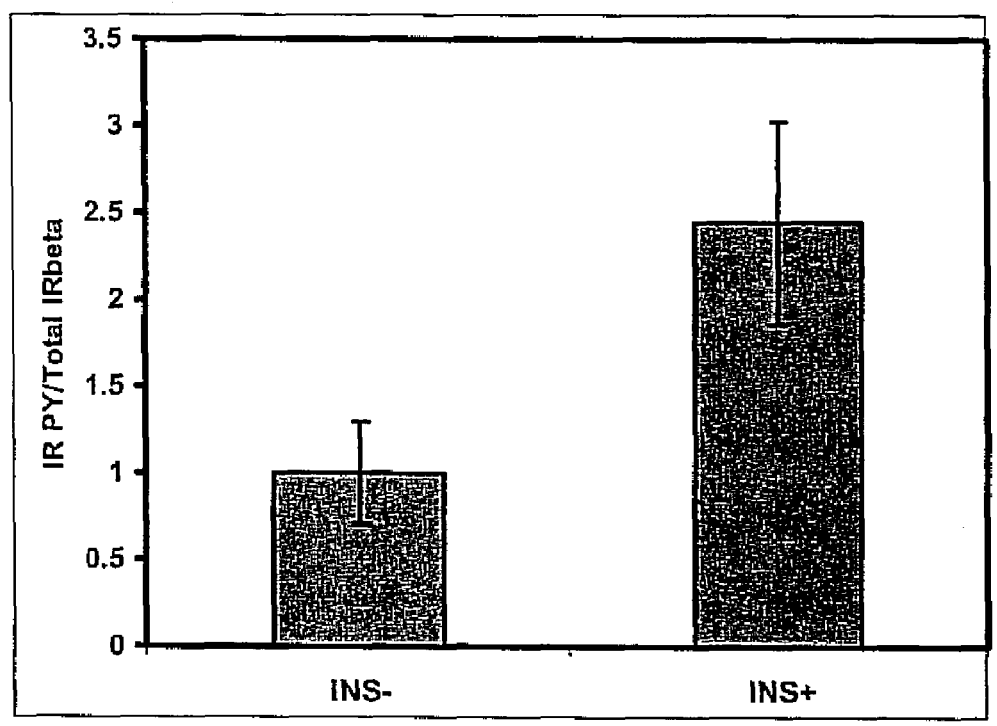
FIG. 8 presents a graph quantifying an immunoblot of insulin receptor tyrosine phosphorylation from retina of an anesthetized rat that received insulin in one eye and vehicle in the other eye.

To demonstrate the efficacy of the methods of this invention, insulin was administered directly to the eye via the subconjunctival space of normal Sprague-Dawley rats. This route of administration bypasses the BRB for a more direct route of insulin action on retina. By injecting serial dilutions of insulin in this manner, it was discovered that a dose of 0.0325 U/100 g insulin activated the IR and Akt kinase pathway without lowering blood glucose values. As shown in FIG. 8, the IRβ is phosphorylated in the eye receiving insulin (right column), compared to the contralateral eye that received vehicle (left column). The retina was processed for IRβ PY content as described in Example 1. The results suggest it is feasible to administer insulin directly to the retina in doses that will not lead to potentially harmful hypoglycemic reactions and potently activate the insulin receptor.

These results demonstrated the in vivo efficacy of periocular insulin administration as a treatment for diabetic retinopathy.

It should be understood that the foregoing disclosure emphasizes certain specific embodiments of the invention and that alternatives equivalent thereto are within the spirit and scope of the invention as set forth in the appended claims.

The invention and the method of making it are now described in such full, clear, concise and exact terms as to enable any person skilled in the art to which it pertains, to make the same. It is to be understood that the foregoing describes preferred embodiments of the present invention and that modifications may be made therein without departing from the spirit or scope of the invention as set forth in the claims.

We claim:

1. A method of treating a nerve-related vision disorder in a non-diabetic subject comprising the step of administering a therapeutically effective amount of a formulation of insulin, to an eye affected by the nerve-related vision disorder in in said subject via a periocular route, wherein the therapeutically effective amount is effective to achieve a local therapeutic effect without a substantial systemic effect.

2. The method of claim 1 wherein the retinal disorder is retinal detachment, retinitis pigmentosa, central retinal artery occlusion, central retinal vein occlusion, ischemic optic neuropathy, high tension glaucoma, low tension glaucoma, or cataract.

3. The method of claim 1, wherein the formulation of insulin, an is administered via a solution, a polymeric base, or a pump.

4. The method of claim 1, wherein the formulation of insulin; an is administered to the eye by a device implanted therein, wherein the device releases the formulation of insulin at a prescribed rate.

* * * * *

UNITED STATES PATENT AND TRADEMARK OFFICE
CERTIFICATE OF CORRECTION

| | | |
|---|---|---|
| PATENT NO. | : 7,829,532 B2 | |
| APPLICATION NO. | : 11/755232 | |
| DATED | : November 9, 2010 | |
| INVENTOR(S) | : Thomas W. Gardner et al. | |

It is certified that error appears in the above-identified patent and that said Letters Patent is hereby corrected as shown below:

At column 3, line number 14, it states "CPY)" where it should state "(PY)".

At column 5, line 65, it states "1nM" where is should state "1mM".

At column 6, line 18, it states "Act" where it should state "Akt".

At column 6, line 45, the word "in" is duplicated.

Signed and Sealed this
Second Day of October, 2012

David J. Kappos
*Director of the United States Patent and Trademark Office*